United States Patent [19]

Danieli

[11] Patent Number: 4,873,965
[45] Date of Patent: Oct. 17, 1989

[54] FLEXIBLE ENDOSCOPE

[76] Inventor: Guido Danieli, 28/A, Viale Filippetti, I-20122 Milano, Italy

[21] Appl. No.: 219,388

[22] Filed: Jul. 15, 1988

[30] Foreign Application Priority Data
Jul. 31, 1987 [IT] Italy .................... 21550 A/87

[51] Int. Cl.$^4$ .............................................. A61B 1/06
[52] U.S. Cl. ............................................ 128/6; 128/4; 138/120
[58] Field of Search .................... 128/4, 6; 138/120

[56] References Cited
U.S. PATENT DOCUMENTS
3,557,780  1/1971  Sato .......................... 128/4

Primary Examiner—William H. Grieb
Attorney, Agent, or Firm—Keil & Weinkauf

[57] ABSTRACT

A flexible endoscope comprising a handle, a flexible section, a terminal articulated length, at least one additional articulated length between the flexible section and the terminal articulated length, each articulated length being movable by two pairs of wires connected with servomechanisms so as to cause the bending of one only or of more articulated lengths simultaneously.

17 Claims, 6 Drawing Sheets

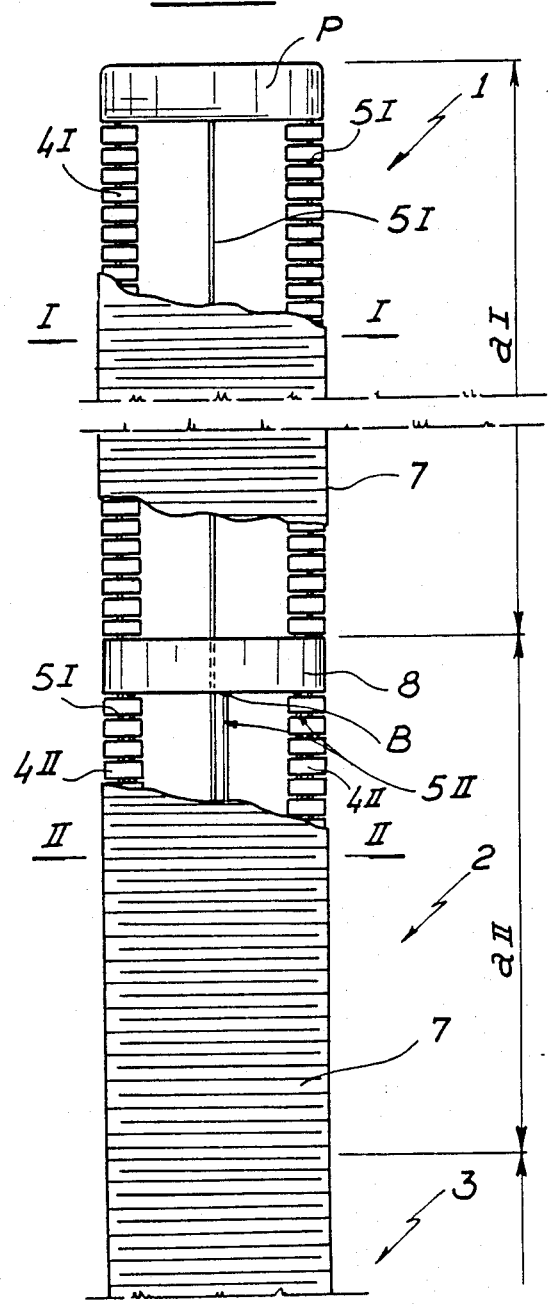
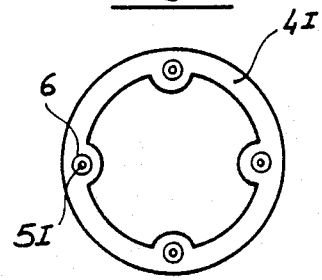
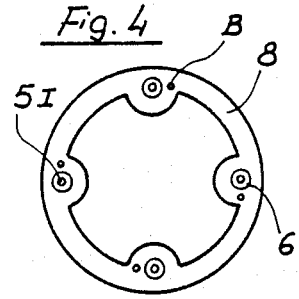
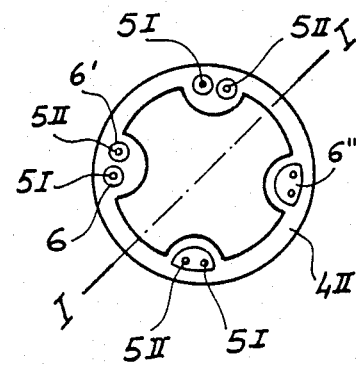

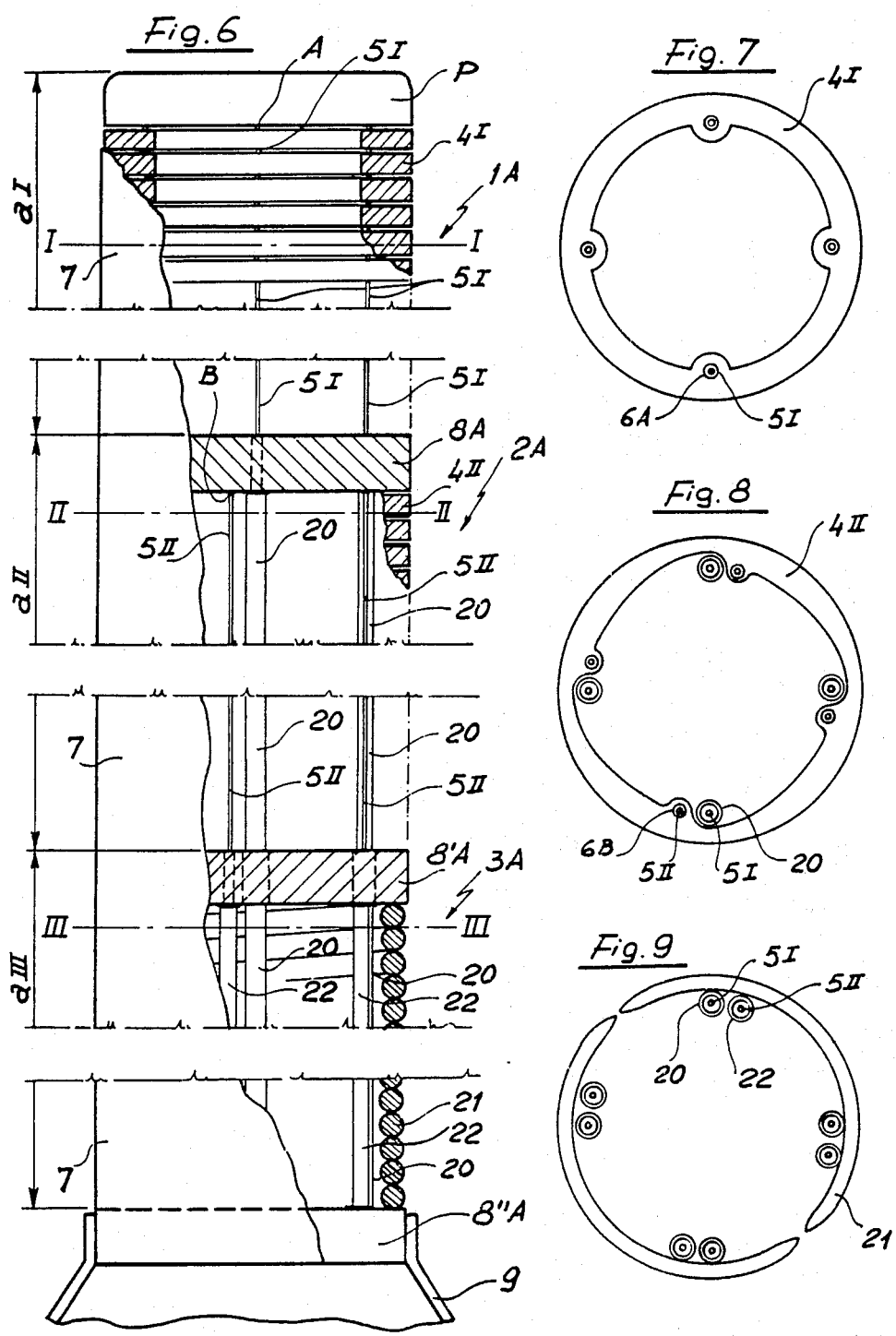

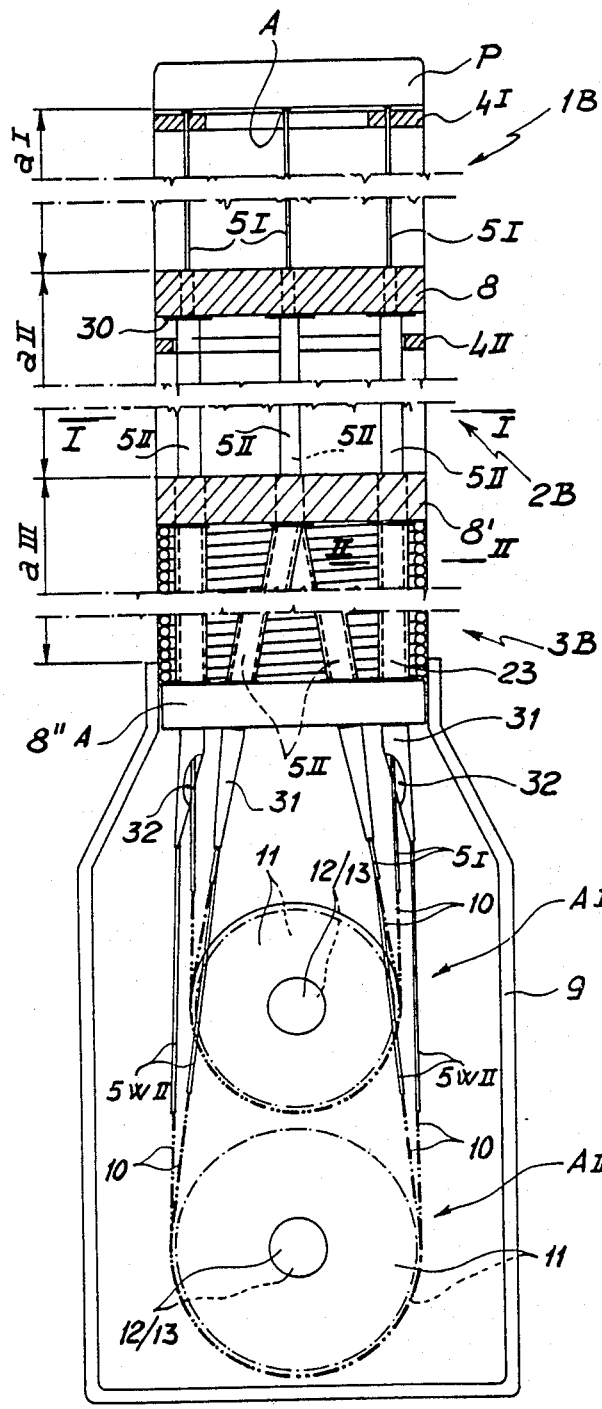
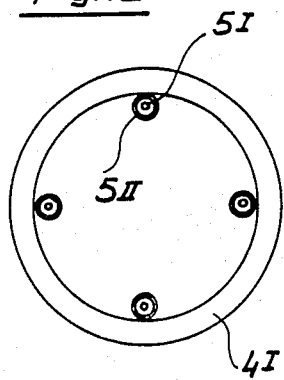
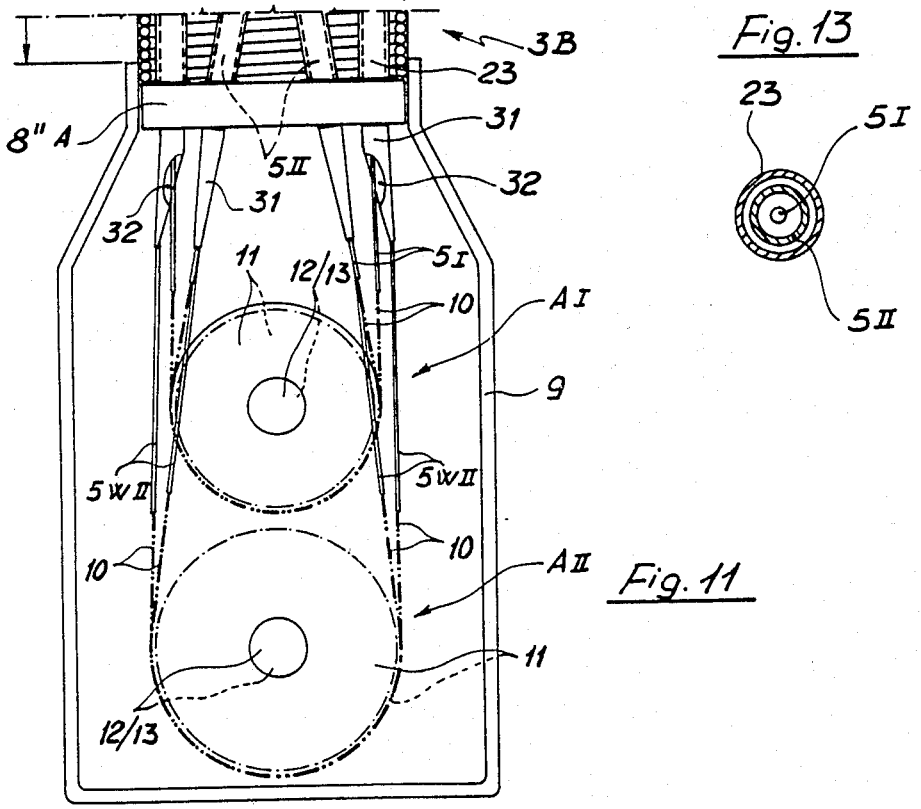
Fig. 12
Fig. 13
Fig. 11

FLEXIBLE ENDOSCOPE

BACKGROUND OF THE INVENTION

This present invention refers to a flexible endoscope.

In particular, a flexible endoscope is here intended to mean an instrument adapted to carry out an optical survey in a cavity of a human body and possible other operations as a biopsy and a cauterizing, although in general it may be also intended as an instrument adapted to carry out observation, checking on, operation of parts of machines, plants and the like.

The prior art comprises flexible endoscopes which transfer the image as taken by an objective on the tip, through a bundle of optic fibers, up to an eye-piece on the outer end or supply the image as taken by a micro-television camera on the tip and transmit it to a monitor. Said endoscopes are articulable by means of a terminal articulated length which, inside and close to the endoscope tip, holds first ends of four wires being part of two pairs of tension wires placed in two right angle planes, each pair of wires having the second ends connected with a motor means placed into the handle of the instrument and manually operable through a knob which is placed on the endoscope handle and rotatable in both directions. For ease of operation, the two knobs are coaxial. The operation is well known and is summarized as follows: the bending of the terminal articulated length in one plane is caused by one knob (e.g. in a vertical plane: bending up and down); the bending of the terminal articulated length in the plane perpendicular to the above plane is caused by the other knob (e.g. in a horizontal plane: bending right and left).

The operation with the known endoscopes, particularly when used in a gastric or intestinal cavity, is difficult because of the proximity of the cavity wall and said endoscopes involve limitations and difficulties in properly positioning the endoscope tip with respect to the operation area.

OBJECT OF THE INVENTION

An object of this present invention is to obviate said difficulties and limitations. The invention, as characterized in the claims, provides an endoscope having an articulated portion with high degree of freedom as well as control means for the movements of said portion.

The advantage of this present invention essentially resides in that the endoscope may be operated very easily, in other words, that a physician who is operating in a rather wide cavity, as a human stomach, easily succeeds in placing the endoscope tip conveniently before the point to be observed or operated on, whatever the position of said point may be and, furthermore, he succeeds to withdraw the endoscope in a manner easy for himself and not detrimental for the patient.

BRIEF DESCRIPTION OF THE DRAWINGS

The invention is set forth herebelow with reference to the drawings which illustrate specific embodiments and wherein:

FIG. 1 is a part view of a first endoscope, partly sectioned;

FIGS. 2 and 3 are, respectively, sectional views along lines I—I and II—II of FIG. 1;

FIG. 4 is a view from the bottom of ring 8 of FIG. 1;

FIG. 6 is a part view of a second endoscope, partly sectioned;

FIGS. 7, 8, 9 are, respectively, sectional views along lines I—I, II—II, III—III of FIG. 6;

FIG. 11 is a view of a third endoscope, partly sectioned;

FIG. 12 is a sectional view along line I—I of FIG. 11;

FIG. 13 is a sectional view along line II—II of FIG. 11;

DESCRIPTION OF THE PREFERRED EMBODIMENTS

Figure 5:
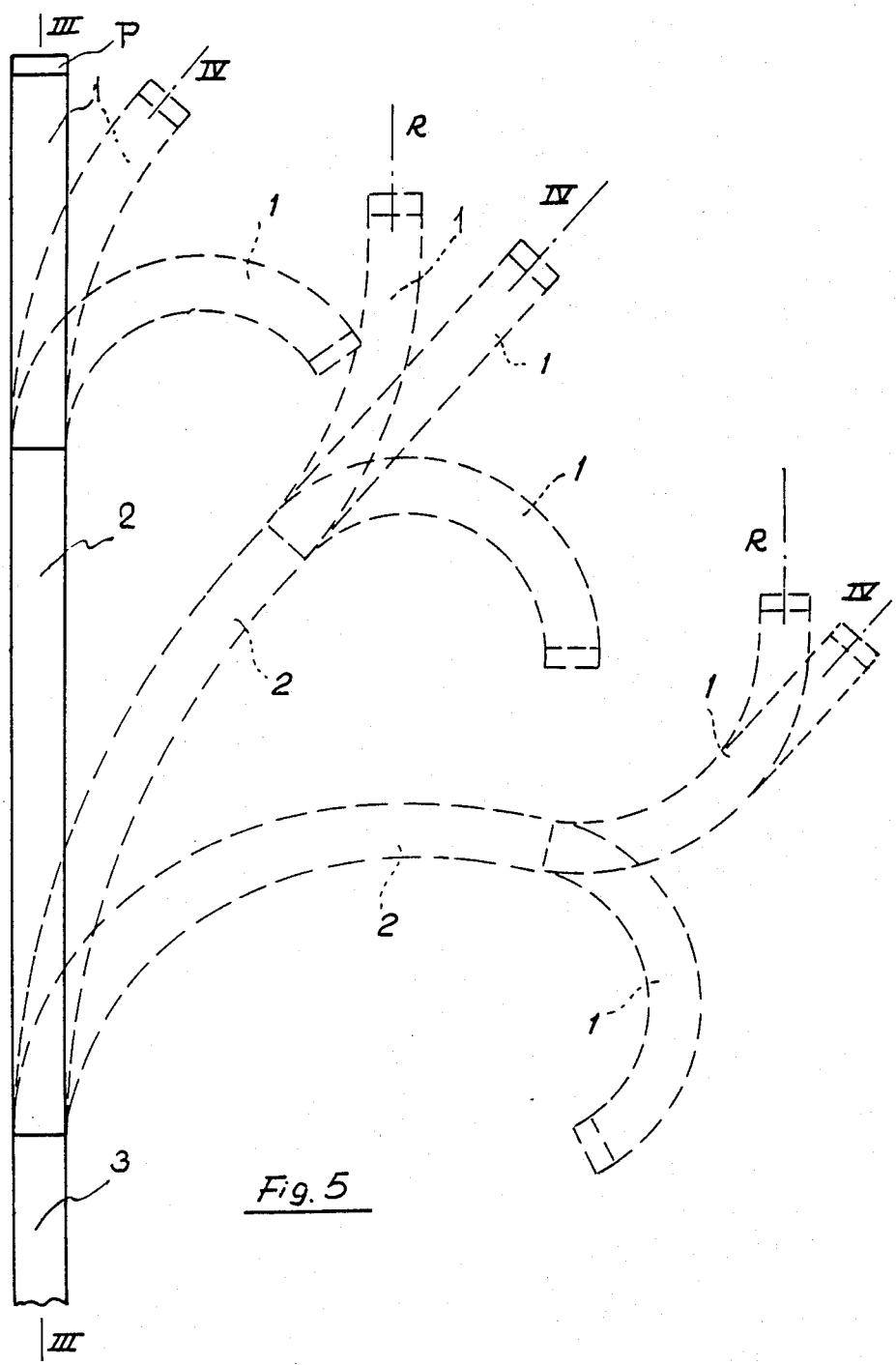
FIG. 5 is a part view showing some positions imparted to the articulated portion of the endoscope.

FIG. 1 shows that the invented endoscope has two articulated lengths 1, 2. The end of the articulated length 1 bears the tip P which incorporates a micro-television camera together with other auxiliary means that are not shown. The portions of the endoscope parts shown in FIG. 1 are made in a known way: the tip P, the plurality of rings 4I as detailed in FIG. 2, one over the other and held and controlled by four steel wires 5I having their upper ends fixed to the periphery of the tip P passing through corresponding holes 6, an outer flexible sheath 7 made of neoprene, shown only in a part of the figure. The articulated length 1 is aI=8 cm, which portion extends from the end of tip P to the upper end of ring 8 that is the first ring of the articulated length 2. The ring 8 has four holes 6, corresponding to the overhanging rings 4, for accommodating the wires 5I, and has the upper ends of other four steel wires 5II fixed to the points B of the lower surface, each wire 5II being positioned to be adjacent to a wire 5I, as visible in FIGS. 3 and 4. FIG. 3 shows two alternative ways to arrange the plurality of rings 4II: on the left side of line I—I a passage 6, 6' is provided for each wire 5I, 5II; on the right side a passage 6" is provided common to two corresponding wires 5I, 5II. The articulated length 2 has an extent of aII=16 cm and is connected in the lower part with a flexible section 3 which is in turn connected with the endoscope handle. The extent of the articulated lengths aI and aII will be in accordance with the objectives of the endoscope.

Each pair of two diametrically opposed wires 5I belongs to a pair of tension wires terminating at control means located at the opposite endoscope end not shown in FIG. 1; said control means will be described later. Nevertheless, it will be realized that, as in known instruments, if in a pair of wires 5I a wire is slackened and the other one is pulled, e.g. the lateral wires in the figure, the articulated length 1 will bend to right or left in the drawing plane; alternatively, if the same operation is carried out with the wires 5I visible in the centre of the figure, then the articulated length 1 will bend in a plane perpendicular to the one of the figure; if two wires are slackened and the other two wires are pulled simultaneously in the two pairs of wires 5I, then the articulated length 1 will bend in a plane within the above mentioned planes. So it will be realized that, if a wire is slackened and the other wire is pulled in one pair of wires 5II, alternatively in the other pair of wires 5II or, simultaneously, in both pairs of wires 5II, then the articulated length 2 will bend as described with reference to the articulated length 1. And then it will be also realized that the combined control of the four pairs of wires 5I, 5II will cause the bending of the articulated length 1 with respect to the articulated length 2 as well as the bending of the latter with respect to the upper end of the flexible part of the endoscope.

In the light of the above, FIG. 5 does not require particular explainations. Attention is only directed to the fact that, among the several combinations of movements which may be imparted to the two articulated lengths 1, 2, there are also those combinations that cause translations of the longitudinal axis of the tip P on lines R parallel with the line III—III of the endoscope in straight position, those which impart to said longitudinal axis positions parallel with a selected line IV and those which maintain for the articulated length 1 the same bend with respect to the articulated length 2, whatever the position of the latter may be.

FIG. 6 diagrammatically shows that part of an articulated two-lengths endoscope which is comprised between the tip P and the juncture of the flexible section 3A with the handle 9; only some of the rings 4I, 4II, respectively in the terminal articulated length 1A and in the additional articulated length 2A, are shown in the figure in order not to complicate the showing thereof. The structure of the flexible section and two articulated lengths is covered by an outer flexible envelope 7 made of neoprene. The structure of the flexible section is a cylinder formed by a steel wire helix 21 comprised between the ring 8'A on the upper end of the flexible section and the ring 8"A at the lower end of said section. Also with the help of FIGS. 7, 8, 9 it is evident that the upper ends of the two first pairs of wires 5I are fastened at A on the lower surface of tip P. Each wire 5I extends into the terminal articulated length 1A through holes 6A in the rings 4I, crosses through the ring 8A and enter a tubular element 20, usually in the form of a steel wire helix, extending beetween the lower wall of said ring 8A and the upper wall of a ring 8"A at the lower end of the flexible section 3A.

The upper ends of the two second pairs of wires 5II are fastened at B on the lower surface of said ring 8A, extend into the additional articulated length 2A through holes 6B, cross through said ring 8'A at the upper end of the flexible section 3A and enter a tubular element 22, in the form of a steel wire helix, extending between the lower wall of said ring 8'A and the upper wall of said ring 8"A. The extent of the articulated lengths and flexible section is aI=8 cm; aII=16 cm; aIII=150 cm, respectively.

Figure 10:
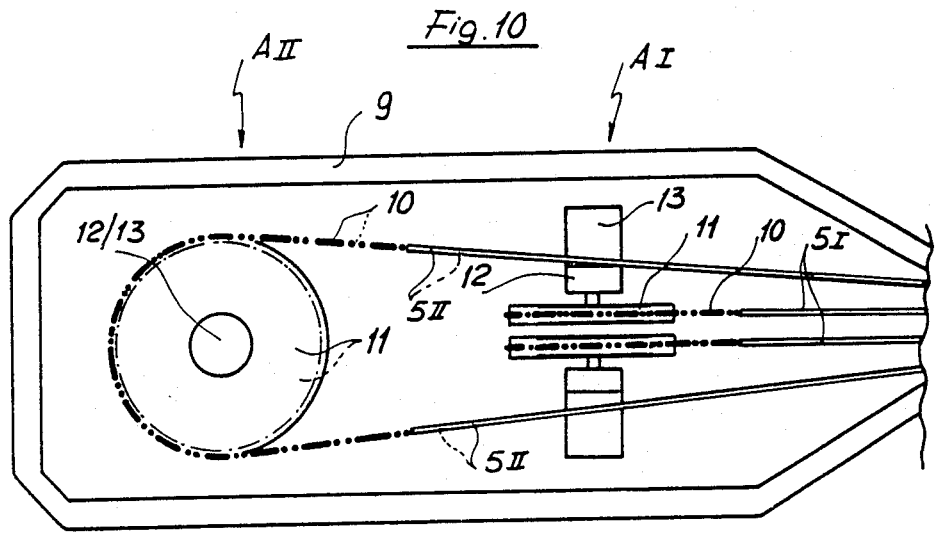
FIG. 10 is a view of control means of the endoscope of FIG. 6.

FIG. 10 shows that the lower ends of the wires 5I and 5II terminate inside the handle 9 of the endoscope. The ends of each pair of wires are fastened at the ends of a chain 10 meshing with a gear wheel 11 moved by a reduction gear 12 in turn moved by a d.c. electrical motor 13. The assembly AI of said motor means controls the two pairs of wires 5I and the assembly AII of said motor means controls the two pairs of wires 5II. The assembly AII in the figure shows only one pair of wires 5II, only one length of chain 10, only one gear wheel 11 and only one motor-reduction gear 12/13, the remaining ones being covered by the above specified parts.

FIG. 11 diagrammatically shows an endoscope still having two articulated lengths, from tip P to handle 9, whilst FIG. 12 is a sectional view along line I—I of FIG. 11. In order not to complicate the figures too much, only a single ring 4I in the terminal articulated length 1B and a single ring 4II in the additional articulated length 2B are shown. For the same reason, the flexible cover completely wrapping the flexible section and the two articulated lengths is omitted. In the endoscope as illustrated herein, each wire of the two pairs of wires 5II by means of which the movements of the additional articulated length 2B are controlled is a flexible tube made of plastic material or other suitable material which extends from the lower surface of the ring 8 upto the entry in the handle 9 and is kept into a tubular element 23 made of plastic material or other suitable material extending between the lower wall of said ring 8' at the top of the flexible length 3B and the upper wall of a ring 8"A at the bottom of said flexible section. FIG. 13 makes clear how, along the flexible section 3B, each wire 5I is within a tubular wire 5II which, in turn, is within a tubular element 23. The objective of the latter is to limit the side movement of wire 5II in the flexible section. The head of each flexible tube has a flange 30 which is rivetted on the lower surface of ring 8. The bottom end of each flexible tube comprises a funnel-shaped element 31 the lower end of which is fastened, directly or by means of a steel wire 5II, to a chain 10 meshing with a gear wheel 11 moved by a d.c. electric motor 12, which can rotate in the two directions, through a speed reduction gear 13 in the assembly of motor means AII. Each funnel-shaped element 31 has an aperture 32 in its own conical wall. Each wire of the two pairs of wires 5I, which control the movements of the terminal articulated length 1B, has the upper end fastened at A on the lower wall of tip P, passes through a hole in the ring 8, enters into the top of a flexible tube 5II and comes out therefrom through the aperture 32 of a funnel-shaped element 31. Each wire 5I has the bottom end directly fastened to a chain 10 in the assembly of motor means AI.

The illustrated assemblies of motor means comprise a gear wheel and a chain meshing with said gear wheel. It will be realized that theese parts may be replaced, respectively, by a pinion and by two racks each of which is connected with the lower end of a wire.

Figure 14:
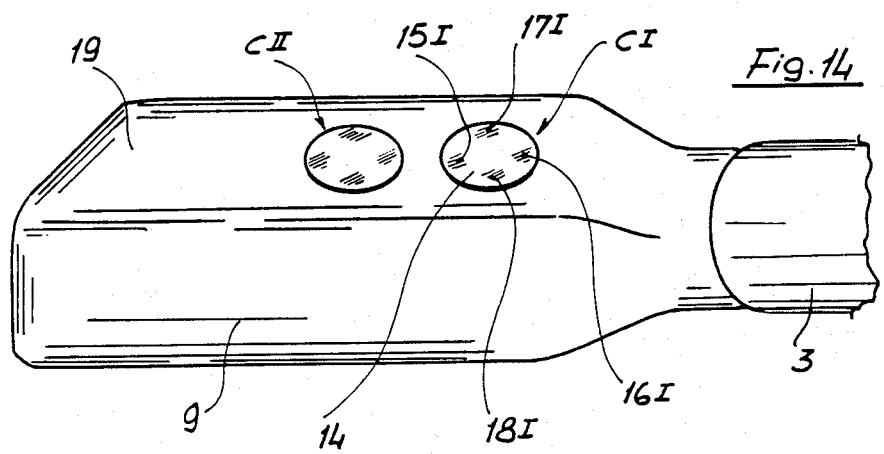
FIG. 14 is a view of the handle of an endoscope.

FIG. 14 shows a pair of control means for the electric motors 13, which pair is located on the face 19 of the handle 9. A control means CI comprises a round cover 14 made of neoprene which covers four push buttons shown by the dashed areas 15I, 16I, 17I, 18I for controlling the motors in the assembly AI by the pressure of a finger. The operation of the control means CII with respect to the assembly AII is identical. If, for example, the button under the area 15I or 16I of the control means CI is pushed, then caused to rotate in one direction or in the opposite direction by that motor 13 which controls the pair of wires 5I that brings about the movement of the articulated length 1 in the plane perpendicular to the handle face 19; if, alternatively, the button 17I or 18I is pushed, then it causes rotation in one direction or in the opposite direction of the other motor 13 in the assembly AI which controls the pair of wires 5I that brings about the movement of the articulated length 1 in a plane parallel with the handle face 19. It will be realized that, if simultaneously a button corresponding to one wire pair and a button corresponding to the other wire pair of one of the control means is pushed, then a movement corresponding to the combination of two movements in perpendicular planes is caused. If the buttons of the control means CII are pushed, then the two wire pairs 5II are moved, identically as described in connection with the control means CI.

Figure 16:
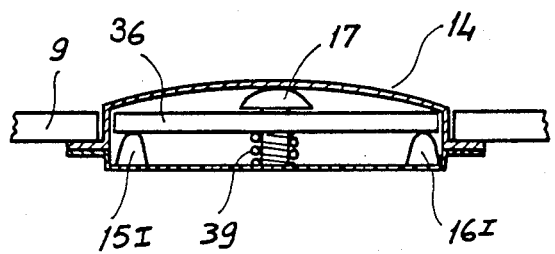
FIG. 16 is a sectional view along line I—I of FIG. 14.
Figure 15:
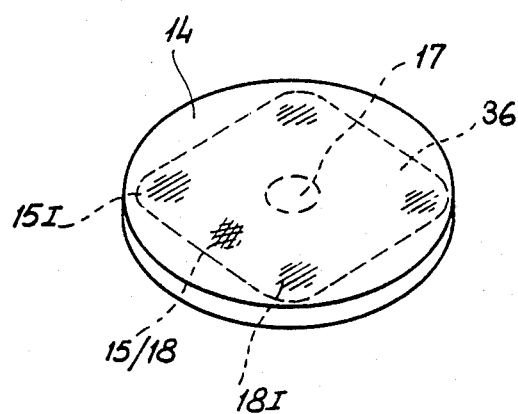
FIG. 15 is the view of the control means of an assembly of motor means in an endoscope.

FIGS. 15 and 16 show a control means similar to the means CI illustrated in FIG. 13, but such that it allows to easily impart to the articulated length corresponding to said control means a movement that is the combination of two movements in perpendicular planes by merely pushing with a finger one single point of the control means. In fact, as illustrated with reference to FIG. 14, again a round cover 14, made of neoprene, covers four buttons 15I, 16I, 17I, 18I, for controlling the two motors in an assembly of control means, and a substantially square small plate 36 held in the cover center by a pin 17. A helical spring 39, around the pin under the small plate 36, biases the latter against the head of the same pin. So, it will be realized that, for instance, if pressure is applied exactly to that vertex of the small plate 36 which corresponds to the button 15I or 18I, then a single movement is imparted to the terminal articulated length; if pressure is applied to a point 15/18, at half the distant between 15I and 18I, then a movement which is the resultant of two perpendicular mevements is imparted to the terminal articulated length.

Figure 17:
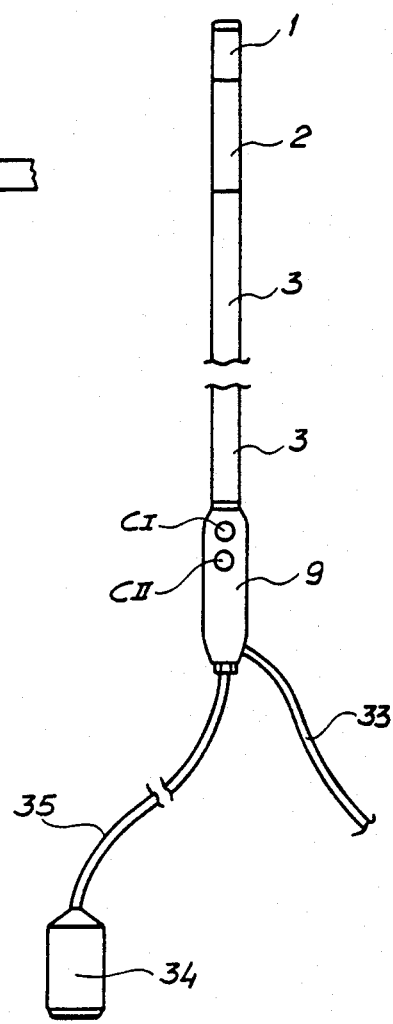
FIG. 17 is a diagrammatic general view of a fourth endoscope.

FIG. 17 illustrates a flexible endoscope wherein the assemblies of motor means (not shown) are received in a box 34 which is kept apart from the endoscope. The latter comprises the articulated lengths 1,2, flexible section 3 and handle 9 incorporating control means CI, CII. The box 34 is connected with the endoscope by means of a neoprene tube 35 wherein the pairs of wires 5I, 5II are passed to move the two articulated lengths and a cable is passed to feed with electric power the four motors of the "direct current torque motor type" which has a low number of revolutions and does not require a speed reduction gear between the motor and the transmission means. The neoprene tube 33 is required to lead into the endoscope electrical cables, a bundle of optic fibers for the lighting means on the endoscope tip, a duct for air blowing, a duct for air sucking, a duct for water and other possible cables and ducts for auxiliary operations.

Modifications in some details of the described endoscope may be made without departing from the spirit of the invention. For instance, the articulated lengths 1, 2 comprise, instead of the plurality of divided rings 4I, 4II, a different structure allowing for an equivalent articulation under the action of the pairs of wires 5I, 5II, that is, a continuous and flexible structure or a discontinuous one wherein the single elements or rings are connected to each other in an articulated manner, so as to form vertebrate lengths which are on the whole articulable in any direction. Moreover, it is obvious that the movement may be imparted to the articulated lengths 1, 2 by conventional motor means which are manually moved, instead of by electrical motors.

I claim:

1. A flexible endoscope comprising a handle for an operator, control means on said handle to operate the endoscope, a flexible section, a first terminal articulated length composed of a plurality of articulated ring elements and controlled by said control means through the medium of motor means and two first pairs of wires passing through holes in said plurality of articulated ring elements, means on the tip of the terminal length for taking images in the cavity where the operation is taking place and for transmitting them to the outside, and means ancillary to the operation of said image-taking means, said ancillary means including
    means for lighting said cavity, and
    means for washing said cavity and said image-taking means,
    wherein said endoscope also comprises, between said flexible section and said terminal articulated length, at least one additional articulated length controlled by a control means on said handle through motor means, and two second pairs of wires, each pair of said wires having the upper end fastened to a ring at the upper end of the additional articulated length and the lower end fastened to a motor means able to pull a wire and slacken the other wire, each motor means for each articulated length being in the form of an assembly comprising a pair of electric motors capable of rotation in both directions of revolution, each associated with means adapted to impart a linear movement, in one direction or in the other one, to the lower ends of a pair of wires, and each assembly of motor means being controlled by an assembly of means located on an outer face of the handle.

2. A flexible endoscope according to claim 1, wherein part of each wire of the two first pairs of wires passes through a tubular flexible element extending between the upper end of the articulated length adjacent to the terminal articulated length and the lower end of the flexible section; and part of each wire of the second pairs of wires passes through a tubular element extending from the upper end to the lower end of said flexible section.

3. A flexible endoscope according to claim 2, wherein the motor means for the articulated lengths are located within the endoscope handle.

4. A flexible endoscope according to claim 2 wherein the motor means for the articulated lengths are received in a box apart from the endoscope.

5. A flexible endoscope according to claim 2, wherein the assembly of means on the outer face of the endoscope handle is an assembly of push buttons, two of said buttons being adapted to impart, alternatively, rotating movement in one direction or in the opposite direction to a first electric motor, two of said buttons being adapted to impart, alternatively, a rotating movement in one direction or in the opposite direction to a second electric motor.

6. A flexible endoscope according to claim 1, wherein each wire of the two second pairs of wires is a tubular flexible and unextensible element having the upper end fastened to the lower wall of said ring at the upper end of the additional articulated length, and the lower end connected with an end of a corresponding transmission element in an assembly of motor means, each of said wires being received in a tubular element extending between a ring at the top of the flexible section and a ring at the bottom of said flexible section, and each wire of the two first pairs of wires passes through an aperture of said ring and, therefrom, into said tubular element to come out at the lower part thereof and fasten to an end of a corresponding transmission element in an assembly of motor means.

7. A flexible endoscope according to claim 6 wherein the motor means for the articulated lengths are located within the endoscope handle.

8. A flexible endoscope according to claim 6 wherein the motor means for the articulated lengths are received in a box apart from the endoscope.

9. A flexible endoscope according to claim 6, wherein the assembly of means on the outer face of the endoscope handle is an assembly of push buttons, two of said buttons being adapted to impart, alternatively, rotating movement in one direction or in the opposite direction to a first electric motor, two of said buttons being adapted to impart, alternatively, a rotating movement in one direction or in the opposite direction to a second electric motor.

10. A flexible endoscope according to claim 1 wherein the motor means for the articulated lengths are located within the endoscope handle.

11. A flexible endoscope according to claim 1 wherein the motor means for the articulated lengths are received in a box apart from the endoscope.

12. A flexible endoscope according to claim 1, wherein the assembly of means on the outer face of the endoscope handle is an assembly of push buttons, two of said buttons being adapted to impart, alternatively, rotating movement in one direction or in the opposite direction to a first electric motor, two of said buttons being adapted to impart, alternatively, a rotating movement in one direction or in the opposite direction to a second electric motor.

13. A flexible endoscope according to claim 1 wherein the ring at the upper end of each additional articulated length has a passage for each wire associated with the overhanging articulated lengths and holds the upper ends of each wire associated with the corresponding additional articulated length.

14. A flexible endoscope according to claim 13, wherein each additional articulated length comprises a plurality of articulated ring elements which carry passages for the wires associated with the terminal articulated length and separate passages for the wires associated with the additional articulated lengths.

15. A flexible endoscope according to claim 1, wherein each additional articulated length comprises a plurality of articulated ring elements which carry passages for the wires associated with the terminal articulated length and separate passages for the wires associated with the additional articulated lengths.

16. A flexible endoscope according to claim 15 wherein each ring element comprised in the additional articulated lengths carries passages for a wire associated with the terminal length and for one wire or wires associated with additional articulated lengths.

17. A flexible endoscope according to claim 1 wherein the wires belonging to the two pairs of wires in the terminal articulated length are adjacent to the wires belonging to the two pairs of wires in the additional articulated lengths so as to provide pairs of wires in a plane perpendicular to other pairs of wires.

* * * * *